United States Patent [19]

Henrick et al.

[11] 3,948,961

[45] Apr. 6, 1976

[54] ORGANIC COMPOSITIONS

[75] Inventors: Clive A. Henrick; Gerardus B. Staal, both of Palo Alto, Calif.

[73] Assignee: Zoecon Corporation, Palo Alto, Calif.

[22] Filed: July 17, 1974

[21] Appl. No.: 489,279

[52] U.S. Cl. ............... 260/410; 260/404; 260/408; 260/468 R; 260/469; 260/473 R; 260/486 R; 260/488 R; 260/476 R; 260/487; 260/484 R

[51] Int. Cl.$^2$ ............................................ C09F 5/08

[58] Field of Search ............ 260/410, 488 R, 486 R, 260/468 R, 476 R, 473 R, 469, 404, 408

[56] References Cited

UNITED STATES PATENTS

| | | | |
|---|---|---|---|
| 3,470,241 | 9/1969 | Eschenmoser | 260/488 R |
| 3,636,018 | 1/1972 | Hejno | 260/410 |
| 3,732,264 | 5/1973 | Baum | 260/410 |
| B350,708 | 1/1975 | Henrick | 260/488 R |

*Primary Examiner*—Winston A. Douglas
*Assistant Examiner*—John F. Niebling
*Attorney, Agent, or Firm*—Donald W. Erickson

[57] ABSTRACT

Cyclopropyl substituted esters, syntheses thereof, compositions thereof, and use for the control of mites and ticks.

10 Claims, No Drawings

ORGANIC COMPOSITIONS

This invention relates to novel compounds, synthesis thereof, compositions thereof, and the control of mites.

The compounds of the present invention are effective for the control of mites and especially spider mites. Spider mites are plant feeders and cause serious damage to orchard trees, field crops, greenhouse plants and other vegetation. The feed on the foliage and fruit of plants and trees and attack a variety of plants and trees due to their wide distribution. Spider mites of the family Tetranychidae, such as *Tetranychus urticae, Tetranychus canadensis, Tetranychus cinnabarinus, Tetranychus pacificus, Bryobia praetiosa, Oligonychus pratensis, Oligonychus ilicis, Panonychus citri, Panonychus ulmi*, and similar related species, are of particular biological interest and economic importance. Other mites are those of the family Tarsonemidae, such as *Steneotarsonemus pallidus*.

Compounds of the present invention of the following formulas I and II are effective control agents for mites.

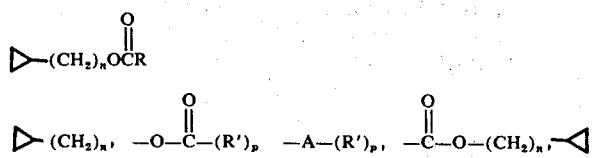

wherein, $n$ is an odd integer of 3 to 13;

$n'$ is an odd integer of 3 to 9;

R is hydrogen, alkyl of one to sixteen carbon atoms, alkenyl of two to 16 carbon atoms, alkynyl of two to 16 carbon atoms, cycloalkyl, aryl, or aralkyl, said cycloalkyl, aryl, or aralkyl being optionally substituted by one or more halogen, alkyl, alkoxy, aryl, aralkyl, aryloxy or aralkoxy groups;

R' is alkylene of one to six carbon atoms or alkenylene of two to six carbon atoms;

$p'$ is zero or one; and

A is alkylene, alkenylene, alkynylene, cycloalkylene of four to six carbon atoms, optionally substituted by one or two alkyl or alkoxy groups; or arylene, optionally substituted by one or two groups selected from alkyl, halogen, or nitro, with the proviso that each compound of formula I contains at least 15 carbon atoms in the molecule.

Hereinafter, each of $n$, $n'$, $p'$, R, R' and A is as defined above unless otherwise specified.

The compounds of formulas I and II are applied to the mite during the egg, larval or nymphal stages in view of their effect in causing inhibition of egg hatching, abnormal development leading to death, inability to pass from one stage to the next, or inability to reproduce. Some of the compounds also exhibit a residual ovicidal effect. A compound of formula I or II can be applied at concentration levels of the order of 0.001 to 1%, usually 0.01 to 0.1% by weight. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of formulas I and II can be prepared by reacting one or two moles, respectively, of the appropriate alcohol ▷—(CH$_2$)$_n$OH with a mono acid of the formula R—COOH or diacid HOOC—(R')$_{p'}$ —A—(R')$_{p'}$ COOH in the presence of an acid catalyst and with heating. The reaction can be carried out in the absence of a solvent; however, use of a solvent inert to the reaction, such as an ether, dichloromethane, chloroform or a hydrocarbon solvent, is preferred. Water may be removed by azeotropic distillation, if desired. RCOHal or HalOC(R')$_{p'}$ —A—(R')$_{p'}$ —COHal may be reacted with ▷—(CH$_2$)$_n$OH in the presence of pyridine and at either room temperature or, if desired, at higher or lower temperature.

The alcohols ▷—(CH$_2$)$_n$OH can be prepared by treating the corresponding acid ▷—(CH$_2$)$_{n-1}$COOH with a reducing agent such as diborane or the corresponding ester with e.g. sodium diethylaluminum hydride. The preparation of the starting materials is shown in copending Ser. No. 461,189 filed Apr. 12, 1974 and Ser. No. 489,207 filed July 17, 1974 the disclosures of which are hereby incorporated by reference. Other well-known conventional methods are equally suitable for the preparation of the alcohols.

The term "alkyl", as used herein, refers to a straight or branched chain saturated aliphatic hydrocarbon group of one to twenty carbon atoms, e.g., methyl, ethyl, propyl, i-propyl, n-butyl, s-butyl, t-butyl, pentyl, hexyl, heptyl, n-octyl, 2-methyloctyl, nonyl, decyl, undecyl, 2-methylundecyl, 6-methylundecyl, dodecyl, pentadecyl and the like. The term "lower alkyl" refers to an alkyl group of one to six carbon atoms.

The term "alkenyl", as used herein, refers to a straight or branched chain unsaturated carbon chain containing two to 20 carbon atoms and having one to three sites of olefinic unsaturation.

The term "alkynyl", as used herein, refers to a straight or branched chain unsaturated carbon chain containing from two to 20 carbon atoms and having one or two sites of acetylenic unsaturation.

The term "cycloalkyl", as used herein, refers to a monovalent cycloalkyl moiety of four to eight carbon atoms, e.g. cyclobutyl, cyclopentyl, cyclohexyl, cycloheptyl, and cyclooctyl.

The term "halogen", as used herein, refers to fluorine, chlorine and bromine.

The term "alkoxy", as used herein, refers to a straight or branched chain saturated aliphatic hydrocarbonoxy group of one to fifteen carbon atoms, e.g., methoxy, ethoxy, n-propoxy, i-propoxy, n-butoxy, i-butoxy, n-heptyloxy, n-dodecyloxy, 2-methyloctyloxy, and the like.

The term "aryl", as used herein, refers to a monovalent aromatic hydrocarbon group containing from six to fourteen carbon atoms such as phenyl, tolyl, xylyl, mesityl, naphthyl, ethylphenyl, t-butylphenyl, and isopropylphenyl.

The term "aralkyl", as used herein, refers to a monovalent hydrocarbon group containing from seven to 15 carbon atoms in which a hydrogen atom of an alkyl group having a chain length of one to six carbon atoms is substituted by an aryl group, such as benzyl, phenethyl, methylbenzyl, naphthylmethyl and naphthylethyl.

The term "aryloxy", as used herein, refers to an oxy-substituted aromatic hydrocarbon group of six to 14 carbon atoms, such as benzyloxy, 2-phenylethoxy, 4methylbenzyloxy, naphthalenemethoxy, naphthyleneethoxy, and the like.

The term "alkylene", as used herein, refers to a bivalent radical derived from a normal or branched chain alkane containing one to 10 carbon atoms by removal of a hydrogen atom from each of two carbon atoms or two hydrogen atoms from one carbon atom.

The term "alkenylene" refers to a bivalent radical derived from a normal or branched chain alkene of two to 10 carbon atoms by removal of a hydrogen atom from each of two carbon atoms or two hydrogen atoms from one carbon atom.

The term "alkynylene" refers to the bivalent alkynylene moiety including branched chain alkynylene, of two to 10 carbon atoms.

The term "cycloalkylene", as used herein, refers to the bivalent cycloalkyl moiety of four to six carbon atoms, i.e. cyclobutylene, cyclopentylene and cyclohexylene.

The term "arylene" refers to any hydrocarbon group of six to 20 carbon atoms and containing at least one aromatic ring, e.g., phenylene or naphthylene, two phenyl or naphthyl rings joined by a single direct bond or by an atom of oxygen, sulfur, or nitrogen, indenylene, fluororenylene, dihydronaphthylene, tetrahydronaphthylene, anthracylene, phenanthrylene, and the like.

The esters of the present invention can be used alone or in an inert carrier substance for the control of mites (Acarina) or can be used in mixture with pesticides and/or juvenile hormone analogs known in the art in oder to obtain a broader spectrum of activity. Suitable insecticides include Baygon, Captan, Sevin, Ciodrin, Systox, Diazinon, Vapona, Galecron, Cygon, Dimethrin, Dursban, Malathion, and Parathion. Typical juvenile hormone analogs which can be used in mixture with the compound of the present invention are described in U.S. Pat. Nos. 3,752,843 and 3,755,411.

The esters of the present invention are useful for the control of mites and ticks which are ectoparasitic on animals and birds. The compounds can be applied in either solution or in powder (dust) form in a conventional manner.

The following examples are provided to illustrate the synthesis of the esters of the present invention and the practice of the present invention. Temperature is in degrees Centigrade. All boiling points were measured by short path distillation.

For those compounds of formula I and II, e.g. the cyclohexane derivatives, where geometrical isomers can exist, each isomer and a mixture of isomers is included unless the isomeric configuration is specifically designated.

EXAMPLE 1

To a solution of 2.48 ml. of a 2.55 M solution of sodium diethylaluminum hydride in 10 ml. toluene under nitrogen is added, at 0°, a solution of 1.22 g. methyl 9-cyclopropylnonanoate in 8 ml. toluene. The reaction mixture is allowed to warm to room temperature and is stirred overnight. An additional 3 ml. of the sodium diethylaluminum hydride is added and the reaction mixture is stirred for 2 hours. To the reaction mixture is added, dropwise, 2N sulfuric acid until gas evolution ceases. The mixture is then taken up in ether/2N sulfuric acid, the ether layer is separated and the aqueous phase is extracted twice with 100 ml. ether. The combined ethereal phases are washed in turn with 50 ml. saturated aqueous ammonium chloride and 50 ml. saturated aqueous sodium chloride, dried over calcium sulfate and the solvent removed by evaporation to yield 0.95 g. 9-cyclopropyl-1-nonanol.

Following the above procedure, the esters of column I are reduced to the corresponding alcohols of column II.

I methyl 7-cyclopropylheptanoate
methyl 11-cyclopropylundecanoate
methyl 13-cyclopropyltridecanoate

II 7-cyclopropyl-1-heptanol
11-cyclopropyl-1-undecanol
13-cyclopropyl-1-tridecanol

EXAMPLE 2

To a solution of 1.14 g. 3-cyclopropylpropionic acid in 50 ml. tetrahydrofuran is added 20 ml. of a 1M solution of diborane in tetrahydrofuran while the temperature is maintained at −10° to −20°. The reaction mixture is stirred at 0° for 30 minutes and then at 20° for 30 minutes. Methanol (1 ml.) is added to destroy any excess diborane and to the reaction mixture is added 30 ml. water and 25 ml. ether. The organic layer is separated and washed, in turn, with water and saturated aqueous sodium chloride, dried over sodium sulfate and the solvent removed by evaporation to yield 3cyclopropyl-1-propanol.

Following the procedure of Example 2, 5-cyclopropyl-pentanoic acid is reduced to 5-cyclopropyl-1-pentanol.

EXAMPLE 3

A mixture of 0.93 g. octanoic acid, 0.695 ml. thionyl chloride and 0.15 ml. dimethylformamide in 10 ml. ether is stirred overnight at room temperature. The ethereal phase of the mixture is separated, the solvent is removed by evaporation and 20 ml. ether is added to the residue. This solution is cooled to 0°, under nitrogen, and 0.95 g. of 9-cyclopropyl-1-nonanol and 0.78 ml. pyridine is added. The reaction mixture is stirred 30 minutes at 0° and then at room temperature for 5 days. The mixture is stirred with 3 equivalents of water for 2 hours at room temperature and then is taken up in ether and washed, in turn, with 2N sulfuric acid (2 × 50 ml.), 10% aqueous sodium carbonate (2 × 50 ml.), water (2 × 50 ml.), saturated aqueous copper sulfate (1 × 50 ml.), water (2 × 50 ml.) and saturated aqueous sodium chloride (1 × 50 ml.). The solution is dried over calcium sulfate, the solvent removed by evaporation and the residue purified by preparative thin layer chromatography (10% ether/hexane) to yield 0.83 g. of 9-cyclopropylnonyl octanoate, b.p. 110° at 0.10 mm.

Following the procedure of Example 3, the alcohols of column II and Examples 1 and 2 are reacted with the acids of column III to yield the esters of this invention such as those listed in column IV.

III acetic acid
propionic acid
butyric acid
pentanoic acid
hexanoic acid
heptanoic acid
octanoic acid
nonanoic acid
decanoic acid
undecanoic acid
dodecanoic acid
tridecanoic acid
tetradecanoic acid
pentadecanoic acid
hexadecanoic acid
heptadecanoic acid

IV 11-cyclopropylundecyl acetate
13-cyclopropyltridecyl acetate
9-cyclopropylnonyl propionate
13-cyclopropyltridecyl propionate
11-cyclopropylundecyl propionate
9-cyclopropylnonyl butyrate
11-cyclopropylundecyl butyrate
7-cyclopropylheptyl pentanoate
9-cyclopropylnonyl pentanoate
13-cyclopropyltridecyl pentanoate
9-cyclopropylnonyl hexanoate
7-cyclopropylheptyl hexanoate
11-cyclopropylundecyl hexanoate
7-cyclopropylheptyl heptanote
9-cyclopropylnonyl heptanoate
11-cyclopropylundecyl heptanoate
5-cyclopropylpentyl octanoate
7-cyclopropylheptyl octanoate
11-cyclopropylundecyl octanoate
5-cyclopropylpentyl nonanoate
7-cyclopropylheptyl nonanoate
9-cyclopropylnonyl nonanoate
3-cyclopropylpropyl decanoate
5-cyclopropylpentyl decanoate
9-cyclopropylnonyl decanoate
3-cyclopropylpropyl undecanoate
7-cyclopropylheptyl undecanoate
9-cyclopropylnonyl undecanoate
3-cyclopropylpropyl dodecanoate
5-cyclopropylpentyl dodecanoate
7-cyclopropylheptyl dodecanoate
5-cyclopropylpentyl tridecanoate
7-cyclopropylheptyl tridecanoate
3-cyclopropylpropyl tetradecanoate
5-cyclopropylpentyl tetradecanoate
3-cyclopropylpropyl pentadecanoate
5-cyclopropylpentyl pentadecanoate
3-cyclopropylpropyl hexadecanoate
5-cyclopropylpentyl hexadecanoate
3-cyclopropylpropyl heptadecanoate
5-cyclopropylpentyl heptadecanoate

EXAMPLE 4

To 30 ml. anhydrous ether and 0.23 g. 10,12-tetradecadien-1-oyl chloride is added 0.1 g. 3-cyclopropyl-1-propanol. The mixture is cooled to 0° and 0.5 ml. pyridine is added. The reaction mixture is stirred for 1 day at room temperature and then is worked up following the procedure of Example 3 to yield 3-cyclopropylpropyl 10,12-tetradecadienoate.

Following the procedure of Example 4, the esters such as those of column VI are prepared from the alcohols of column II and Examples 1 and 2 and the acid chlorides of column V.

V 2-decynoyl chloride
7,10-pentadecadienoyl chloride
7-dodecynoyl chloride
cis-4-decenoyl chloride
3-methyl-3-decenoyl chloride
cis-7-dodecenoyl chloride
trans-2,trans-4-decadienoyl chloride
2,4-dodecadienoyl chloride
cis-4-tetradecenoyl chloride
trans-3-hexadecenoyl chloride
cyclohexanecarbonyl chloride
2-naphthalenecarbonyl chloride
4-chlorocinnamoyl chloride
cinnamoyl chloride
4-methycinnamoyl chloride
4-octyloxycinnamoyl chloride
4-chlorobenzoyl chloride
benzoyl chloride
2-phenylacetyl chloride
cyclopentanecarbonyl chloride
4-chlorocyclohexanecarbonyl chloride
4-methoxycyclohexanecarbonyl chloride
4-phenylbenzoyl chloride

VI 5-cyclopropylpentyl 2-decynoate
3-cyclopropylpropyl 7,10-pentadecadienoate
7-cyclopropylheptyl 7-dodecynoate
9-cyclopropylnonyl cis-4-decenoate
7-cyclopropylheptyl cis-4-decenoate
7-cyclopropylheptyl 3-methyl-3-decenoate
7-cyclopropylheptyl cis-7-dodecenoate
5-cyclopropylpentyl cis-7-dodecenoate
5-cyclopropylpentyl trans-2,trans-4-decadienoate
7-cyclopropylheptyl 2,4-dodecadienoate
3-cyclopropylpropyl cis-4-tetradecenoate
3-cyclopropylpropyl trans-3-hexadecenoate
11-cyclopropylundecyl cyclohexanecarboxylate
9-cyclopropylnonyl 2-naphthalenecarboxylate
13-cyclopropyltridecyl 4-chlorocinnamate
7-cyclopropylheptyl cinnamate
11-cyclopropylundecyl 4-methylcinnamate
9-cyclopropylnonyl 4-octyloxycinnamate
7-cyclopropylheptyl 4-chlorobenzoate
5-cyclopropylpentyl 2-phenylacetate
9-cyclopropylnonyl cyclopentanecarboxylate
9-cyclopropylnonyl 4-chlorocyclohexane
11-cyclopropylundecyl 2-methoxyhexane
5-cyclopropylpentyl 4-phenylbenzoate

EXAMPLE 5

A. To 0.59 g. succinic acid is added 23.4 g. phosphorus pentachloride. After the initial reaction subsides the mixture is heated until refluxing begins. After all the solid dissolves, the mixture is maintained at reflux for 15 minutes. Phosphorus oxychloride is then removed by distillation at reduced pressure and succinyl chloride is separated by collecting the fraction boiling at 90°/20 mm.

B. To the succinyl chloride obtained in (A) above is added 30 ml. anhydrous ether and 1.0 g. 7-cyclopropylheptanol. The mixture is cooled to 0° and 2 ml. pyridine is added. The reaction mixture is stirred for 1 day at room temperature and then is worked up following the procedure of Example 3 to yield bis(7-cyclopropylheptyl) succinate.

Following the procedure of Example 5, the alcohols of column II and Examples 1 and 2 are reacted with the acids of column VII to yield the esters of this invention such as those listed in column VIII.

VII malonic acid
glutaric acid
adipic acid
fumaric acid
maleic acid
itaconic acid
muconic acid
acetylenedicarboxylic acid
2-hexene-1,6-dicarboxylic acid
4-octene-1,8-dicarboxylic acid
1,3-hexadiene-1,6-dicarboxylic acid
diacetylenedicarboxylic acid
terephthalic acid
1,4-cyclohexanedicarboxylic acid
2,7-naphthalenedicarboxylic acid
thiodiphenyl-4,4'-dicarboxylic acid
biphenyl-4,4'-dicarboxylic acid
oxydiphenyl-4,4'-dicarboxylic acid
2-chloro-1,4-benzenedicarboxylic acid
2,5-dinitro-1,4-benzenedicarboxylic acid
2-ethyl-1,4-benzenedicarboxylic acid
2-bromo-1,4-benzenedicarboxylic acid
1,4-cyclohexanediacetic acid
1,3-cyclopentanediacetic acid
1,4-cycloheptanedicarboxylic acid
2-chloro-1,4-cyclohexanedicarboxylic acid
2-methyl-1,4-cyclohexanediacetic acid

VIII bis(3-cyclopropylpropyl) malonate
bis(5-cyclopropylpentyl) malonate
bis(9-cyclopropylnonyl) glutarate
bis(3-cyclopropylpropyl) adipate
bis(7-cyclopropylheptyl) fumarate
bis(3-cyclopropylpropyl) maleate
bis(9-cyclopropylnonyl) itaconate
bis(7-cyclopropylheptyl) muconate
bis(5-cyclopropylpentyl) acetylenedicarboxylate
bis(7-cyclpropylheptyl) 2-hexane-1,6-dicarboxylate
bis(3-cyclopropylpropyl) 4-octene-1,8-dicarboxylate
bis(5-cyclopropylpentyl) 1,3-hexadiene-1,6-dicarboxylate
bis(9-cyclopropylnonyl) diacetylenedicarboxylate
bis(7-cyclopropylheptyl) terephthalate
bis(5-cyclopropylpentyl) cyclohexanedicarboxylate
bis(3-cyclopropylpropyl) 2,7-naphthalenedicarboxylate
bis(3-cyclopropylpropyl) thiodiphenyl-4,4'-dicarboxylate
bis(3-cyclopropylpropyl) biphenyl-4,4'-dicarboxylate
bis(3-cyclopropylpropyl) oxydiphenyl-4,4'-dicarboxylate
bis(7-cyclopropylheptyl) 2-chloro-1,4-benzenedicarboxylate
bis(7-cyclopropylheptyl) 2,5-dinitro-1,4-benzenedicarboxylate
bis(5-cyclopropylpentyl) 2-ethyl-1,4-benzenedicarboxylate
bis(5-cyclopropylpentyl) 2-bromo-1,4-benzenedicarboxylate
bis(3-cyclopropylpropyl) 1,4-cyclohexanediacetate
bis(3-cyclopropylpropyl) 1,3-cyclopentanediacetate
bis(3-cyclopropylpropyl) 1,4-cycloheptanedicarboxylate
bis(5-cyclopropylpentyl) 2-chloro-1,4-cyclohexanedicarboxylate
bis(7-cyclopropylheptyl) 2-methyl-1,4-cyclohexanediacetate A wettable powder suitable for field application after dilution can be formulated by blending and then air-milling a mixture of 20 to 30% of an ester of this invention, 60 to 70% of a solid carrier such as Attaclay X-250, 1 to 3% of an anionic surfactant, such as Igepon T-77, and 3 to 5% of a dispersing agent such as Marasperse N-22.

A typical formulation is as follows:

| | |
|---|---|
| Active ingredient[1] | 25.0% |
| Synthetic calcium silicate | 40.0% |
| Attapulgite Clay | 29.0% |
| Sodium lignosulfonate | 4.0% |
| Sodium N-methyl N-oleoyl taurate | 2.0% |

[1]The active ingredient is selected from one or more of the following:
9-cyclopropylnonyl octanoate
bis(3-cyclopropylpropyl) terephthalate
bis(5-cyclopropylpentyl) 1,4-cyclohexanedicarboxylate The mite control agents of the present invention can be used alone in an inert agriculturally acceptable carrier substance for the control of mites (Arachnids) or can be used in mixture with insecticides and/or juvenile hormone analogs known in the art to provide a broader spectrum of activity on more developmental stages of the mites or on other pestiferous insect species.

The effectiveness of the compounds of the present invention is demonstrated below.

Adults (*Tetranychus urticae*) are allowed to oviposit for 24 hours on lima bean leaf discs (diameter 1 cm.) on moist cottonwool.

After 24 hours, the adults are removed and the leaf discs are then dipped in acetone solutions of the compound being tested.

After submersion for 1 second, the solvent on the leaf discs is allowed to dry and the leaf discs are then glued to a plastic petri dish to prevent crumpling.

Six days later (when all the eggs on untreated discs have merged), the number of unhatched eggs is calculated as a percentage of the total number originally present, corrected for any spontaneous non-emergence observed in control discs treated only with solvent (Abbott correction).

Table IV presents the results of biological testing conducted as outlined above.

TABLE IV

| Compound | % concentration in solution | % hatching prevented |
| --- | --- | --- |
| 9-cyclopropylnonyl octanoate | 0.1 | 100 |

What is claimed is:

1. Compounds of formula I:

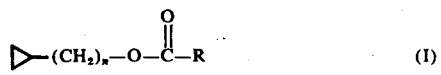

wherein, n is an odd integer of 3 to 13 and

R is hydrogen, alkyl of one to 16 carbon atoms, alkenyl of two to 16 carbon atoms, alkynyl of two to 16 carbon atoms, cycloalkyl of four to eight carbon atoms, aryl of six to 14 carbon atoms, aralkyl of seven to 15 carbon atoms, said cycoalkyl, aryl or aralkyl being optionally sustituted by one or more halogen, alkyl, alkoxy, aryl, aralkyl, aryloxy or aralkoxy groups, with the proviso that each compound of formula I contains at least 15 carbon atoms in the molecule.

2. Compounds according to claim 1 wherein R is alkyl of two to sixteen carbon atoms.

3. Compounds according to claim 1 wherein the total number of carbon atoms in the molecule is from 17 to 24 and R is alkyl of two to 16 carbon atoms, alkenyl of two to 16 carbon atoms, alkynyl of two to 16 carbon atoms, cyclohexyl, phenyl or benzyl, said cyclohexyl, phenyl or benzyl being optionally substituted by one or two groups selected from chloro, methyl, ethyl, methoxy, ethoxy and phenyl.

4. Compounds according to claim 2 wherein R is alkyl of two to 16 carbon atoms and n is an odd integer of 3 to 9.

5. The compound, 9-cyclopropylnonyl octanoate, according to claim 4.

6. The compound, 5-cyclopropylpentyl dodecanoate, according to claim 4.

7. The compound, 5-cyclopropylpentyl hexadecanoate, according to claim 4.

8. The compound, 3-cyclopropylpropyl tetradecanoate, according to claim 4.

9. The compound, 3-cyclopropylpropyl hexadecanoate, according to claim 4.

10. The compound, 5-cyclopropylpentyl decanoate, according to claim 4.

* * * * *